(12) United States Patent
Tisinger et al.

(10) Patent No.: US 6,649,401 B2
(45) Date of Patent: Nov. 18, 2003

(54) GRAM-POSITIVE FATTY ACID DEGRADER

(76) Inventors: Jessi Lind Tisinger, 1424 Penn Rd., Floyd, VA (US) 24091; David Joseph Drahos, 6014 Scotford Ct., Roanoke, VA (US) 24018; Jonathan Leder, 3801 Goose Creek Valley Rd., Montvale, VA (US) 24122; Domenic Anthony Paone, 7992 Forest Creek, Roanoke, VA (US) 24018

( * ) Notice: Subject to any disclaimer, the term of this patent is extended or adjusted under 35 U.S.C. 154(b) by 60 days.

(21) Appl. No.: 09/861,142

(22) Filed: May 18, 2001

(65) Prior Publication Data

US 2003/0049832 A1 Mar. 13, 2003

(51) Int. Cl.$^7$ .................................................. C12N 1/20

(52) U.S. Cl. ................................. 435/252.5; 435/252.4; 435/244; 424/93.46; 424/93.3

(58) Field of Search .......................... 435/252.5, 252.4, 435/244; 424/93.46, 93.3

(56) References Cited

U.S. PATENT DOCUMENTS 6,066,494 A * 5/2000 Hsieh .......................... 435/263

\* cited by examiner

*Primary Examiner*—Irene Marx
(74) *Attorney, Agent, or Firm*—Mishrilal Jain

(57) ABSTRACT

The invention discloses a Gram-positive microorganism, *Bacillus megaterium,* that effectively and efficiently degrades fats, oils and grease. A composition comprising said microorganism and a method for degrading fatty acids and grease are also disclosed.

7 Claims, 2 Drawing Sheets

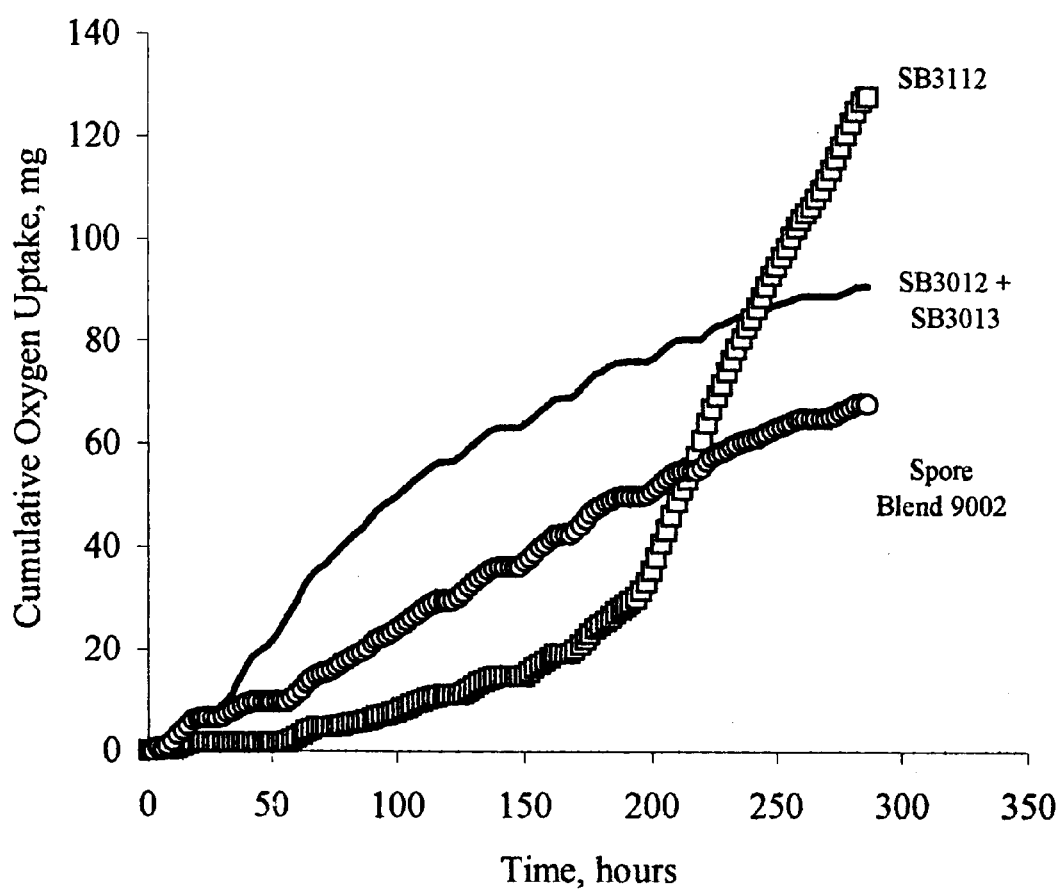
Figure 1. The efficacy of SB3112 and various microorganisms to degrade grease.

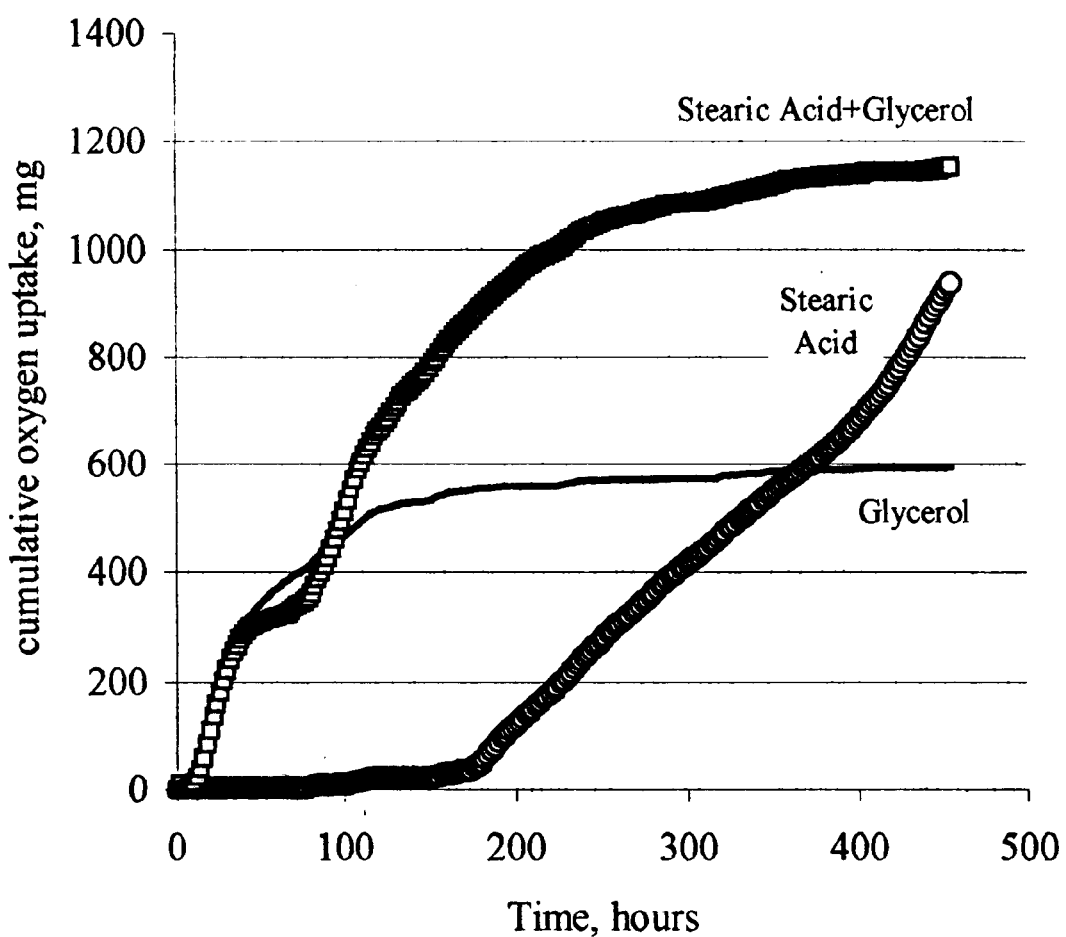
Figure 2. The effect of glycerol on biodegrading activity of SB3112.

GRAM-POSITIVE FATTY ACID DEGRADER

FIELD OF THE INVENTION

The present invention is related to identifying a Gram-positive organism that degrades fats, oils and grease. More particularly, the present invention is related to providing a non-pathogenic, spore-forming Gram-positive, lipophilic bacterial strain that produces extracellular lipase and also efficiently oxidizes or degrades fatty acids and grease. The invention is further related to a formulation comprising said Gram-positive organism.

BACKGROUND

Most food service establishments are required to have a device that prevents grease from flowing directly from the kitchen or food preparation area into the sewer or to an on-site waste disposal system. Commonly called grease traps, these devices function to physically prevent oils and grease from flowing directly into the sanitary sewer and to store the separated grease solid for eventual solid waste disposal.

Many municipalities place restrictions and surcharges based on the biological oxygen demand (BOD), and oil and grease (O&G) levels in the effluents from grease traps. In addition to wastewater treatment costs and surcharges, the grease solids from the traps must also be periodically removed and disposed. The food service establishment then faces two recurring charges for wastewater treatment, one a municipal treatment cost and secondly a grease disposal cost.

However, the frequency of pumping the accumulated grease solids can be quite variable, ranging from several weeks to several months. If traps are not cleaned on a regular basis, grease clogs may occur causing wastewater to back up into the food preparation area causing malodors and requiring the establishment to close until the problem is corrected. In addition to providing physical means to trap O&G, grease traps can function to biologically mediate a reduction of BOD and O&G in the bulk liquid resulting in cleaner effluent wastewater. This reduction of BOD and O&G is dependent upon the hydraulic retention time, which is dependent on the size of the grease trap and wastewater flow. Other factors that affect biological activity within a grease trap include pH, temperature and whether or not the facility practices bioaugmentation.

Bioaugmentation, the addition of commercial bacterial products that increase the biological activity in the system, has been used to reduce the BOD and O&G in the effluents from grease traps. This has helped to reduce surcharges that the food establishments must pay to municipalities for wastewater services. Additionally, bioaugmentation has been used to decrease the pumping frequency of grease traps, to keep drain lines open and to reduce malodors.

In addition to grease traps, bioaugmentation has also been used to help remove grease from lift stations, drain lines, septic tanks and other situations where grease accumulation can cause flow problems and malodors.

Bioaugmentation products can be either liquid or dry. Because of ease of handling, liquid products are generally preferred and added by a liquid metering pump drawing on a container that is replenished on a periodic basis.

Strains used in bioaugmentation of grease applications produce an important extracellular enzyme, lipase. This enzyme hydrolyzes and breaks the ester bond between the glycerol backbone and the fatty acid moieties making up the grease. The glycerol is relatively easily disposed by biodegradation, However the fatty acids are difficult to degrade and can persist causing pH drops, clogging and malodors.

When Gram-negative microorganisms are used for bio-augmentation in liquid products, they are present as vegetative cells and as such, they may be killed by chemicals, such as surfactants and preservatives, which are often used in such formulations. Therefore, products containing Gram-negative organisms cannot contain biocides and surfactants. Then, unpreserved liquid products may develop severe malodors from microbial contaminants growing in the product. Some of these contaminants may be undesirable in a food service environment. Furthermore, unpreserved products may also suffer from decreased shelf life and efficacy. Clearly, while Gram-negative microorganisms have an advantage in fatty acid degradation, their use in residential and food service products have serious drawbacks.

Dry Gram-negative products, on the other hand, do have a slight advantage of improved shelf life over liquid Gram-negative formulations. However, this advantage is only marginal and varies significantly from strain to strain. Disadvantages of dry products include contaminating dust and difficulty in handling dry materials. Although dry products can be rehydrated with water and applied like liquid products, the disadvantages of using unpreserved liquids containing Gram-negative microorganisms still apply to rehydrated dry materials.

Many Gram-negative microorganisms are known to have the ability to biodegrade fatty acids generated by the action of lipase. This ability to oxidize and degrade fatty acids is generally not found in Gram-positive, spore-forming microorganisms, specifically members of the genus Bacillus.

Accordingly, there is a need to develop bioaugmented formulations that can effectively and efficiently degrade or oxidize fats, oil and grease without causing malodors or other undesirable conditions, such as occurs with Gram-negative organisms.

Specifically, there is a need to find non-pathogenic, spore-forming Gram-positive, lipophilic bacterial strain that produces extracellular lipase and efficiently oxidizes or breaks down fatty acids and grease. Heretofore, such a Gram-positive organism and a formulation containing the same have not been identified or produced.

SUMMARY OF THE INVENTION

It is, therefore, an object of the present invention to provide a non-pathogenic, spore-forming Gram-positive, lipophilic bacterial strain that produces extracellular lipase and also efficiently hydrolyzes or degrades fatty acids and grease or a mixture of fatty acid and grease It is a further object of the present invention to provide a composition comprising a non-pathogenic, spore-forming Gram-positive, lipophilic bacterial strain that produces extracellular lipase and efficiently hydrolyzes or degrades fats, oils and grease.

An additional object of the present invention is to provide a method for degrading fatty acid and grease using a Gram-positive strain of Bacillus species.

Yet another object of the present invention is to enhance the biodegrading activity of Gram-positive strain of Bacillus species.

Various other objects and advantages of the present invention will become evident from a brief description of the drawings and detailed description of the invention.

Additional advantages and novel features of the invention will be set forth in part in the description that follows, and in part will become more apparent to those skilled in the art upon examination of the following or upon learning by practice of the invention.

BRIEF DESCRIPTION OF THE DRAWINGS

In the drawings, FIG. 1 shows the efficacy of various microorganisms to degrade grease; and FIG. 2 shows the effect of glycerol on biodegrading activity of SB-3112.

DETAILED DESCRIPTION OF THE INVENTION

The above and various other objects and advantages of the present invention are achieved by a biologically pure culture of a Gram-positive microorganism, *Bacillus megaterium*, strain SB-3112, having the identifying characteristics of ATCC deposit number PTA-3142, and a composition comprising the same. The deposit shall be maintained in viable condition at the ATCC during the entire term of the issued patent and shall be made available to any person or entity for non-commercial use without restriction, but in accordance with the provisions of the law governing the deposit.

It should be understood that unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the methods and materials described herein are preferred. Unless mentioned otherwise, the techniques employed or contemplated herein are standard methodologies well known to one of ordinary skill in the art. The materials, methods and examples are only exemplary and not limiting.

The term "biodegradation", "biodegraded", or "biodegrading" as used herein means that the substrate is broken down, oxidized or degraded by the microorganism. And the term "activity enhancement" as used herein means that the biodegradation activity of the microorganism is increased by the presence or addition of a particular component, said component being designated as "activity enhancer", or "activator".

By utilizing a Gram-positive, spore-forming organism that can oxidize fatty acids, one can obtain the advantages of an improved preserved liquid product. Unlike Gram-negative containing products, the preserved, spore-based Gram-positive containing product can contain preservatives and surfactants to aid in the biodegradation of fats, oils or grease, because the spores are relatively resistant to biocides and surfactants. Furthermore, these products may also contain micronutrients promoting the growth of the microorganisms. Thus, a Gram-positive product comprising lipase-producing, fatty acid degrading, spore-forming microorganism in a preserved liquid formulation offers various advantages required for efficacious degradation of oil and grease.

Liquid products formulated in accordance with the present invention for grease traps, or other similar uses where fatty acid or grease needs to be degraded, may also contain in addition to surfactants, biocides, growth promoting non-toxic amounts of inorganic nutrients and micronutrients, certain activity enhancers, stabilizers, viscosifiers and the like. Table 1 lists examples of various components that a formulation may contain in addition to SB3112 in accordance with the present invention.

Other inclusions in the formulation are exemplified below:

(A) Other microorganisms may be selected from the group consisting of the genera Acinetobacter, Aspergillus, Azospirillum, Burkholderia, Bacillus, Ceriporiopsis, Enterobacter, Escherichia, Lactobacillus, Paenebacillus, Paracoccus, Pseudomonas, Rhodococcus, Syphingomonas, Streptococcus, Thiobacillus, Trichoderma, and Xanthomonas.

(B) Within Bacillus genera, the microorganism may be selected from the group consisting of *Bacillus licheniformis, Bacillus amyoliquofaciens, Bacillus laevolacticus,* and *Bacillus pasteurii* and a combination thereof.

(C) The preservative is selected from the group consisting of 1,2-benzisothiazolin-3-one;5-chloro-2-methyl-4-isothiazolin-3-one, 2-methyl-4-isothiazolin-3-one; quaternium-15; phenol; sodium o-phenylphenate; o-phenylphenol; 6-acetoxy-2,4-dimethyl-m-dioxane; tris(hydroxymethyl)nitromethane; hexahydro-1,3,5-tris (2-hydroxyethyl)-s-triazine; chlorhexidine; p-hydroxybenzoic acid or its methyl, ethyl, propyl, or butyl esters; benzoic, ascorbic, citric, or sorbic acid; imidazolidinyl urea; diazolidinyl urea; dimethylol dimethylhydantoin; methylene bisthiocyanate; 2-bromo-2-nitropropane-1,3-diol; 1,2-benzisothiazoline-3-one; methyl anthranilate and a mixture thereof.

(D) The surfactant is selected from the group consisting of trideceth-3; 3 mole ethylene oxide adduct of a linear, primary C12–14 alcohol; 7 mole ethylene oxide adduct of a linear, primary C12–14 alcohol; sodium lauryl sulfate; ammonium lauryl sulfate; dodecyl benzene sulfonic acid; ammonium lauryl sulfate; sodium xylene sulfonate; sodium lauryl sulfate; cocamide diethanolamine; lauramine oxide; sodium alphasulfo methyl C12–18 ester and disodium alphasulfo C12–18 fatty acid salt; sodium dodecylbenzene sulfonate; alkyl polyglycoside; nonylphenoxypoly (ethyleneoxy) ethanol, branched; nonylphenoxypoly (ethyleneoxy) ethanol, branched; alkoxylated linear alcohol; blend of ethoxylates of linear, primary 12–14 carbon number alcohol; octylphenoxypolyethoxyethanol absorbed on magnesium carbonate; sodium dodecylbenzene sulfonate and isopropyl alcohol; poe (6) tridecyl alcohol; poly (oxy-1, 2-ethanediyl), alpha (nonylphenyl)-omega hydroxy, branched, and a mixture thereof (E) The range (v/v) in which various components may be included in the composition in accordance with the present invention are as follows
  (i) SB3112 ranging from about $1\times10^5$ to about $1\times10^9$ CFU/ml
  (ii) glycerol ranging from about 0.01% to about 10%
  (iii) surfactant ranging from 0.1 to 10%
  (iv) preservative ranging from I ppm to 1.0%
  (v) color ranging from 0.02% to 1%
  (vi) fragrance ranging from 0.02% to 1.0%
  (vii) viscosifier ranging from 0.05% to 5%

Superiority of SB3112

In order to show unexpectedly significant superiority of SB3112 over other *Bacillus megaterium* strains, the following side-by-side comparative study was performed using three other *Bacillus megaterium* strains having designations Strain 1, Strain 2 and Strain 3. Stearic acid (SA) and glycerol (G) were used as substrates. Stearic acid degradation was determined by standard respirometric (oxygen uptake) measurement and sterile techniques were used in all studies.

A CES AER-200 respirometer unit was used. The 500 ml respirometer bottles contained $SSC_3$ minimal salt medium and 20 mM MOPS adjusted to pH 7.2. Respirometer bottles were prepared by adding $SSC_3$ mineral salt media to each bottle. This media contained the following chemicals per liter of water: $NH_4Cl$, 0.8g; $MgSO_4.7H_2O$, 0.2 g; $CaCl_2.2H_2O$, 10 mg, $Fe_2Na_2$Ethylene diamine ditetraacetic acid, 15 mg; $KH_2PO_4$, 3.06 g; $FeSO_4.7H_2O$, 28 µg; $ZnSO_4.7H_2O$, 140 µg; $MnSO4.H_2O$, 84 µg; $CoCl_2.6H_2O$, 24 µg; $CuSO_4.5H_2O$, 25 µg; $NaMoO_4.2H_2O$, 24 µg. The buffer, 3-N-morpholino) propane sulfonic acid (MOPS), was added 4.28 g per liter. The pH of the medium was adjusted to 7.0 prior to autoclaving. The bottles containing $SSC_3$ media were autoclaved for two hours.

The target substrate, 1000 ppm stearic acid (SA), was added as indicated below. The SA was weighed and added individually into the appropriate reactor. Glycerol, 500 ppmv, was added to all bottles. Glycerol was first diluted 50% v/v with deionized water to reduce the viscosity and 0.5 ml was added to each reactor. A pure culture of microorganism was used as inoculum. The optical density (OD) of an overnight culture in plate count broth (PCB) was determined in order to estimate the bacterial count. The target dose into each reactor was $1 \times 10^6$ CFU/ml based on the optical density measurement of the broth culture. MacConkey streaks were performed on the inoculum prior to its use to detect Gram-negative contamination. MacConkey and standard methods agar (SMA) plate streaks were also performed on each bottle's contents at the end of the experiment (MacConkey agar plates were used to detect Gram-negative contamination; SMA plates were used to test for pure cultures).

The Treatments (in duplicate) were as follows

Glycerol+SB3112
Glycerol+Stearic acid +SB3112
Glycerol+Strain 1
Glycerol+Stearic acid +Strain 1
Glycerol+Strain 2
Glycerol+Stearic acid +Strain 2
Glycerol+Strain 3
Glycerol+Stearic acid +Strain 3

As indicated above, all cultures were tested with stearic acid plus glycerol. A glycerol only control was also monitored for each individual strain.

The values for stearic acid degradation lag phase, oxygen uptake rate, and the total cumulative oxygen uptake for each strain are presented in Table 1. The oxygen uptake rates were calculated using a three-point average and the maximum values are shown in Table 2. The data clearly indicate surprising results, showing that SB3112 is superior, demonstrating the highest activity on stearic acid by having the shortest lag phase, the fastest uptake rate and the greatest cumulative oxygen uptake, compared to all other strains tested.

Efficacy of SB3112 for Degrading Various Fatty Acids

Having determined the superiority of SB3112 compared to other *Bacillus megaterium* strains, the following study was performed to determine the efficacy of SB3112 for degrading fatty acids. For this purpose, a number of fatty acids (99% or greater purity) were obtained from commercial sources as listed below:

stearic acid, C-18
palmitic acid, C-16
valeric acid, C-5
butyric acid, C-4
acetic acid, C-2

Respirometric (oxygen uptake) activity was used to measure the ability of SB3112 to degrade fatty acids.

A CES AER-200 respirometer unit was used to monitor oxygen uptake in 500 ml bottles maintained at 25° C. Each 500 ml bottle contained $SSC_3$ minimal salt medium and 20 mM MOPS buffer (pH adjusted to 7.2). Glycerol, 500 ppmv, was added to all bottles. Glycerol was first diluted 50% v/v with deionized water to reduce the viscosity and 0.5 ml was added to each reactor. High molecular weight fatty acids (C-16 and C-18) were weighed individually and added to the appropriate bottles to a 1000 mg/L concentration. The low molecular weight fatty acids (C-2, C-4 and C-5) were filter sterilized using chemical resistant filters (0.2 µm) and were added to the appropriate autoclaved bottles to provide 1000 mg/L concentration.

A pure culture of SB3112 was used as inoculum. The optical density (OD) of an overnight culture in plate count broth (PCB) was determined in order to estimate the bacterial count. The target dose into each reactor was $1 \times 10^6$ CFU/ml based on the optical density measurement of the broth culture. MacConkey streaks were performed on the inoculum at the time of use to detect Gram-negative contamination. Sterile techniques were used in all experiments. Treatments (numbers show triplicates as indicated below)

| | |
|---|---|
| 1, 2, 3. | Glycerol only control |
| 4, 5, 6. | C-18 |
| 7, 8, 9. | C-16 |
| 10, 11, 12. | C-5 |
| 13, 14, 15. | C-4 |
| 16, 17, 18. | C-2 |

(C represents carbon chain length)

MacConkey and standard methods agar (SMA) agar streaks were performed on each bottle's contents at the end of the experiment. The MacConkey agar plates were used to detect Gram-negative contamination. The SMA plates were used to test for pure culture. No contamination was detected.

Oxygen uptake response attributed to the individual fatty acid was calculated by subtracting the glycerol data from the fatty acid plus glycerol data, in order to observe the amount of oxygen uptake attributed to the oxidation of the fatty acid alone. The pH of each reactor at the end of the experiment was within the range of 6.8 to 7.2. Standard Methods Agar (SMA) plates were streaked from each bottle. All bottles showed single colony morphologies on SMA plates at the end of the experiment indicating that pure culture testing was achieved. Final MacConkey streaks of all bottles were negative (no Gram-negative contamination).

Table 3 shows the activity of SB3112 for degrading various fatty acids. The oxygen uptake rates were calculated using a three-point running average and the maximum value is shown in Table 2. The results indicate that SB3112 degrades (oxidizes) all these fatty acids (stearic, palmitic, valeric, butyric and acetic acids). It may be noted that valeric and butyric acids are particularly odorous, and because SB3112 degrades these compounds, SB3112 may be useful in reducing odors attributable to these fatty acids.

Efficacy of SB3112 to Degrade Grease

The following study was performed to show the efficacy of SB3112 to degrade grease.

Respirometer bottles were prepared by adding 250 ml of SSC$_3$ mineral salt media to each bottle. The pH of the medium was adjusted to 7.0 prior to autoclaving. The bottles containing SSC$_3$ media were autoclaved for two hours. Waste kitchen grease was autoclaved separately to kill unwanted microorganisms. Following autoclaving of the grease, 2 ml of the hot sterile grease was added to each cooled 250 ml respirometer bottle. The inoculum for the respirometer bottles was an overnight broth culture (plate count broth) of each strain, or the 9002 blend of microorganisms. Each bottle was inoculated to contain initially ≈3×10$^5$ CFU/ml. Following inoculation a caustic trap containing 5 ml of 30% KOH to remove carbon dioxide was suspended in the bottle and the septum cap was secured tightly.

To show superiority of SB3112, a comparative study was performed using two other inoculum samples. Thus, the three inoculum were as follows:

1. *Bacillus megaterium* strain SB3112.
2. Inoculum 9002, representing a blend of four spores (*Bacillus licheniformis, Bacillus amyloliquefaciens, Bacillus pasteurii,* and *Bacillus laevolacticus*) that produce extracellular enzymes lipase, amylase and protease. This mixture is known to affect the degradation of kitchen waste materials, but does not degrade fatty acids.
3. Inoculum SB3012 and SB3013 representing a blend of Gram-negative microorganisms known for their ability to degrade fatty acids.

Following inoculation, the bottles containing the SSC$_3$ media, waste kitchen grease, and the inoculum were placed into the respirometer water bath (23° C.). Each bottle was then connected to a respirometer port. Consumption of oxygen was monitored continuously by the respirometer.

The results of this experiment are shown in FIG. 1. The data show that the Gram-negative microorganism mixture (SB 3012 and 3013) began consuming oxygen almost immediately at a rate of 1.5 mg O$_2$/L/hr. The 9002 spore blend also began consuming oxygen quickly, but the rate of 1.2 mg O$_2$/L/hr was slightly lower than SB3012 and SB3013. Strain SB3112 had a lag of 50 hr before oxygen consumption began at the rate of 0.5 mg O$_2$/L/hr. At about 180 hr, SB3112 began a rapid rise in oxygen consumption surpassing both the spore blend 9002 and the Gram-negative blend. The rate of oxygen consumption by SB3112 after 180 hr was 4.4 mg O$_2$/L/hr compared to 0.7 and 0.8 mg O$_2$/L/hr for SB3012/3013 and 9002, respectively, during the same time period. Uninoculated controls did not show oxygen uptake (data not shown).

Effect of Glycerol on Biodegrading Activity of SB-3112

As shown by the following study, it was discovered that the presence of glycerol enhances the biodegrading activity of SB3112.

SB3112 culture was obtained from retained slant and plated on agar by standard method. A single colony was picked then grown overnight in standard plate count broth. Based on the measured optical density, 1×10$^6$ CFU/ml (target) of SB3112 was added to each reactor. Each substrate (stearic acid and glycerol) was disinfected by heating to 80° C. and added to the reaction vessel. The reactor size was 500 ml containing SSC$_3$ autoclaved medium.

Treatments (in duplicate)

1, 2. Stearic acid, 0.2%, heated/melted (0.5 ml per 500 ml reactor).

3, 4. Stearic acid, 0.2%+0.1% glycerol (0.5 ml heated per 500 ml reactor).

5, 6. Glycerol, 0.1%.

Final MacConkey streaks were performed to detect any Gram-negative contamination. No contamination was found. The results are shown in FIG. 2. The data clearly indicate that fatty acid degrading activity of SB3112 is significantly enhanced by the presence or addition of glycerol.

Various embodiments of the present invention have now been described in accordance with the objects and advantages noted above. It will be appreciated that these examples are merely illustrative and not limiting of the invention. Of course, many variations and modifications of the present invention will be apparent and suggested to those of ordinary skill in the art and all such variations and modifications are included within the purview and scope of the claims.

TABLE 1

OPTIONAL COMPONENTS IN A COMPOSITION ACCORDING TO PRESENT INVENTION.

| | Quantity Range | Preferred Amount |
|---|---|---|
| Component | | |
| Surfactants | | |
| Alkyl benzene sulfonic acid | 0.5–5% | 1–2% |
| Ethoxylated alcohol | 0.5–5% | 0.5–1.5% |
| 1,2 benzisothiazolin 3 one (preservative) | 0.025–0.2% | 0.045–0.1% |
| Methyl anthranilate (preserves spore state) | 20–40 ppm | 25–35 ppm |
| Microorganisms | | |
| *Bacillus licheniformis* | 1 × 10$^6$–1 × 10$^9$ CFU/ml | 5 × 10$^6$–1 × 10$^8$ CFU/ml |
| *Bacillus amyloliquefaciens* | 1 × 10$^6$–1 × 10$^9$ CFU/ml | 5 × 10$^6$–1 × 10$^8$ CFU/ml |
| *Bacillus pasteurii* | 1 × 10$^6$–1 × 10$^9$ CFU/ml | 5 × 10$^6$–1 × 10$^8$ CFU/ml |
| *Bacillus laevolacticus* | 1 × 10$^6$–1 × 10$^9$ CFU/ml | 5 × 10$^6$–1 × 10$^8$ CFU/ml |
| Optional ingredients | | |
| Tetrasodium ethylenediamine tetraacetate (stabilizer) | 0.1–1.0% | 0.2–0.5% |

TABLE 1-continued

OPTIONAL COMPONENTS IN A COMPOSITION ACCORDING TO PRESENT INVENTION.

| | Quantity Range | Preferred Amount |
|---|---|---|
| Fragrance | 0.1–0.5% | 0.2–0.3% |
| Other spore forming microroganisms | $1 \times 10^6$–$1 \times 10^9$ CFU/ml | $5 \times 10^6$–$1 \times 10^8$ CFU/ml |
| Acrysol TT615 (viscosifier) | 0.1–0.5%[1] | 0.2–0.3%[1] |

[1]Amount depends on the composition ingredients and viscosity desired.

TABLE 2

Stearic acid utilization by various *Bacillus megaterium* strains.

| | SB3112 | Strain 1 | Strain 2 | Strain 3 |
|---|---|---|---|---|
| Lag phase (hours) | 20 | 72 | 60 | 100 |
| Oxygen uptake rate (mg/hr) | 1.9 | 1.1 | 0.8 | 0.9 |
| Total cumulative oxygen uptake (mg) | 180 | 140 | 110 | 90 |

Each reactor volume was 0.5 liters.

TABLE 3

Degradation of fatty acids by *Bacillus megaterium* strain SB3112.

| Fatty acid used | Oxygen uptake rate (mg/hr) | Total cumulative oxygen uptake (mg) |
|---|---|---|
| stearic acid, C-18 | 0.98 | 83 |
| palmitic acid, C-16 | 2.87 | 480 |
| valeric acid, C-5 | 2.37 | 342 |
| butyric acid, C-4 | 1.96 | 308 |
| acetic acid, C-2 | 1.7 | 247 |

Each reactor volume was 0.5 liters.

What is claimed is:

1. A biologically pure culture of *Bacillus megaterium* having all of the characteristics of strain SB-3112, ATCC PTA-3142.

2. A composition comprising *Bacillus megaterium* having all of the characteristics of strain SB-3112, ATCC PTA-3142, and a component selected from the group consisting of a non-toxic nutrient formulation, surfactant, activator, preservative, filler, stabilizer, fragrance, viscosifier, enzymes, and a combination thereof.

3. The composition of claim 2, further comprising additional classes of bacteria.

4. The composition of claim 3, wherein the additional classes of bacteria are selected from the group consisting of genera: Acinetobacter, Aspergillus, Azospirillum, Burkholderia, Bacillus, Ceriporiopsis, Enterobacter, Escherichia, Lactobacillus, Paenebacillus, Paracoccus, Pseudomonas, Rhodococcus, Syphingomonas, Streptococcus, Thiobacillus, Trichoderma, Xanthomonas, and a combination thereof.

5. The composition of claim 3, wherein the bacteria are selected from the group consisting of *Bacillus licheniformis, Bacillus amyoliquofaciens, Bacillus laevolacticus, Bacillus pasteurii, Bacillus subtilus, Bacillus megaterium* and a combination thereof.

6. The composition of claim 2, wherein said activator is glycerol.

7. The composition of claim 2, wherein the components are as follows:
 (i) *Bacillus megaterium* SB3112, ATCC PTA-3142, ranging from about $1 \times 10^5$ to about $1 \times 10^9$ CFU/ml;
 (ii) glycerol ranging from anout 0.01% to about 10%;
 (iii) surfactant ranging from 0.1 to 10%;
 (iv) preservative ranging from 1 ppm to 1.0%;
 (v) color ranging from 0.02% to 1%;
 (vi) fragrance ranging from 0.02% to 1.0%;
 (vii) viscosifier ranging from 0.05% to 5%; all percentages being v/v.

* * * * *